(12) United States Patent
Zastrow (10) Patent No.: US 11,154,309 B2
(45) Date of Patent: Oct. 26, 2021

(54) SURGICAL INSTRUMENT

(71) Applicant: Frank Zastrow, Heidelberg (DE)

(72) Inventor: Frank Zastrow, Heidelberg (DE)

(*) Notice: Subject to any disclaimer, the term of this patent is extended or adjusted under 35 U.S.C. 154(b) by 258 days.

(21) Appl. No.: 16/346,375

(22) PCT Filed: Sep. 19, 2017

(86) PCT No.: PCT/DE2017/200097
§ 371 (c)(1),
(2) Date: Apr. 30, 2019

(87) PCT Pub. No.: WO2018/077354
PCT Pub. Date: May 3, 2018

(65) Prior Publication Data
US 2020/0060696 A1    Feb. 27, 2020

(30) Foreign Application Priority Data

Oct. 31, 2016 (DE) .......................... 102016120755.1

(51) Int. Cl.
*A61B 17/16* (2006.01)
*A61C 1/08* (2006.01)

(52) U.S. Cl.
CPC ...... *A61B 17/1673* (2013.01); *A61B 17/1633* (2013.01); *A61B 17/1637* (2013.01); *A61B 17/1635* (2013.01); *A61C 1/08* (2013.01)

(58) Field of Classification Search
CPC ............ A61B 17/1633; A61B 17/1635; A61B 17/1637; A61B 17/1673; A61B 17/32002; A61B 17/320016; A61B 2017/320024; A61C 1/08; A61C 1/082; A61C 8/0039; A61C 8/0089; Y10S 408/703
See application file for complete search history.

(56) References Cited

U.S. PATENT DOCUMENTS 4,071,030 A    1/1978  Hedrick
5,078,605 A *  1/1992  Sutter ............... A61B 17/1644
                                                      408/59

(Continued)

FOREIGN PATENT DOCUMENTS

DE    20 2011 004 267 U1    6/2011
EP        0 083 558 A2       7/1983

(Continued)

OTHER PUBLICATIONS

International Search Report for Application No. PCT/DE2017/200097, dated Jan. 3, 2018.

(Continued)

*Primary Examiner* — Anu Ramana
(74) *Attorney, Agent, or Firm* — Seed Intellectual Property Law Group LLP (57) ABSTRACT

A surgical instrument, in particular for use in dental surgery, includes a machining device and a protector device. The machining device has a shaft with a connection region and a hollow cylindrical head, wherein an active region, in particular for machining and/or for grinding of bone, is formed at a distal edge of the head. The protector device surrounds the head, at least in regions, and is rotatably coupled with a bearing element of the machining device extending, at least in regions, inside of the head.

12 Claims, 10 Drawing Sheets

(56) References Cited

U.S. PATENT DOCUMENTS

| | | | |
|---|---|---|---|
| 8,113,833 B2* | 2/2012 | Courvoisier | B23B 51/04 433/165 |
| 9,962,170 B2* | 5/2018 | Jansen | A61B 17/1615 |
| 2007/0042324 A1 | 2/2007 | Florman | |
| 2008/0249553 A1 | 10/2008 | Gruber et al. | |

FOREIGN PATENT DOCUMENTS

| | | |
|---|---|---|
| WO | 2008/088105 A1 | 7/2008 |
| WO | 2011/026164 A1 | 3/2011 |

OTHER PUBLICATIONS

Written Opinion for Application No. PCT/DE2017/200097, dated Jan. 3, 2018.

* cited by examiner

SURGICAL INSTRUMENT

BACKGROUND

Technical Field

The present disclosure relates to a surgical instrument, in particular for use in dental surgery.

Description of the Related Art

Dentists performing surgeries, oral surgeons, and maxillofacial surgeons are often faced with the challenge that bone has been lost in the oral cavity as a result of bone atrophy, accidents, periodontitis, or tooth extraction.

When dental implants are planned in order to insert new teeth, it is important that these bone deficits be constructed before or at the same time the implant is placed, so that the dental implants once again have a new foundation and a stable support.

Autologous bone is still considered to be the gold standard in bone grafting procedures. This is due to the properties of the bone, since autologous bone combines osteogenic, osteoinductive, and osteoconductive properties. This means that the bone has the potency to generate its own bone tissue and form its own vessels; in addition, it acts as a guide structure for newly generated bone. In contrast to autologous bone, bone replacement material does not have any biological potency and therefore acts only osteoconductively, i.e., it also acts as a guide rail.

Various methods for working with autologous bone are already known. In the case of larger bone deficits, toothless bone areas basically lend themselves as secondary intraoral extraction points, with the maxillary tuberosity, the anterior nasal spine, the palate, the region of the maxillary sinus wall in the upper jaw or the lower jaw as alternatives, since they are of a rather cortical nature, and the bone quality is considered to be very good and stable. There are various bone extraction points in the lower jaw, e.g., toothless areas, the chin, or the retromolar region.

The bone extraction may in this case take place using various instruments. The concept of the bone extraction is mostly similar here.

Three to four predetermined breaking points are created using either a so-called Lindemann bur or a piezosurgery device, or, alternatively, a small saw, and the block is subsequently extracted using a chisel or another instrument. This is disadvantageous in that a somewhat extensive force needs to be applied to the jaw during bone extraction. Therefore, this procedure is somewhat dreaded by the physician, also because this hammering or breaking free of the bone block from the respective region is also uncomfortable for the patient.

Dentists are accustomed to rotary instruments and drills because of their profession. Thus, use of the so-called trephine bur or hollow bur, which is put on a handpiece and has a head that is designed as a hollow cylinder, has also become established in this way. Teeth for machining the bone are formed on the distal edge of the head. Trephine burs are used, for example, for implant bed preparation and have a diameter of approximately 3 mm to 4 mm. Using these burs, extremely small and narrow drilling cylinders are removed, which are only conditionally suitable for bone construction.

In the case of the aforementioned devices, approximately three to four cuts or predetermined breaking points must be created for the bone extraction in order to obtain the necessary piece of bone. This causes great stress for the patient and requires great technical skill on the part of the surgeon. In the process, it must, in particular, be ensured that the surrounding soft tissue, e.g., the cheek or lip, is not injured by the surgical tool.

BRIEF SUMMARY AND GENERAL DESCRIPTION

The present disclosure provides a surgical instrument designed and developed in such a way that reliable bone extraction that is gentle for the patient is possible with structurally simple means.

The present disclosure relates to a surgical instrument, in particular for use in dental surgery, comprising a machining device and a protector device, wherein the machining device comprises a shaft with a connection region and a hollow cylindrical head, wherein an operating area, particularly for machining and/or grinding bone is formed at a distal edge of the head, wherein the protector device surrounds the head, at least in regions, and wherein the protector device is rotatably coupled to a bearing element of the machining device extending, at least partially, within the head.

According to the disclosure, it has been recognized that the underlying design can be achieved, in a surprisingly simple way, by means of the combination of a machining device, in particular a trephine bur, and a protector device. For this purpose, the machining device has a shaft with a connection region and a hollow cylindrical head. The connection region can be used for connection to a surgical handheld device, for example a common elbow or handpiece, as is used by dentists or dental surgeons. Furthermore, the distal edge of the head is designed as an active region, in particular for machining bone. For example, the distal edge may have cutting or sawing teeth and/or a diamond tip.

In a manner further according to the disclosure, it has been found that the protecting device can be rotatably coupled to the head or the machining device in a particularly safe and simple manner in that the machining device has a bearing element extending, at least in regions, within the head. It is thus possible to machine bone at the extraction site with the distal edge of a machining device rotated by a medical handheld device, while the protector device remains at least substantially stationary, namely due to the pivotal connection between the protector device and machining device. Thus, the surrounding tissue is ideally protected from injuries.

In doing so, it is specifically conceivable for the bearing element to extend in the axial direction, in particular from the bottom of the head at least to the distal edge of the head. The protector device can be coupled to the free end of the bearing element. The bearing element does not necessarily have to extend up to the distal edge in the axial direction, provided the protector device projects a corresponding distance into the head in order to be rotatably coupled to the bearing element. More advantageously, the bearing element extends, in the axial direction, beyond the distal edge of the head such that the connection between the protector device and machining device is implemented outside of the head. In particular, it is conceivable for the bearing element to be formed in the shape of a pin and to engage the protector device in a corresponding region.

In a particularly advantageous manner, the protector device surrounds the head such that only a circular arc of the distal edge serves as the active region. Contrary to a preconception of a person skilled in the art, it has been recognized that a machining device with a head designed as a hollow cylinder, which has an active region for machining bone, is not only suitable for removing small drill cylinders. Instead, an appropriately designed machining device can be used to "cut away" the required piece of bone or bone segment from the bone. The special arrangement and configuration of the protector device means that only a circular arc of the distal edge of the head can be placed into contact with the bone and thus serve as an effective active region. As a result of this design, it is possible for surgeons to "peel off" an approximately crescent-shaped bone piece from the bone that is usable for bone construction. In contrast to the instruments and tools known from the prior art, there is no need to create three to four cuts and/or predetermined breaking points. Instead, only a single predetermined breaking point—for example apical—results; a hammering-out of the bone is not necessary. The resulting block can then be extracted or luxated without applying extensive force, which is much more gentle and comfortable for the patient compared to the known devices and techniques. The protector device advantageously surrounds the head in such a way that a circular segment formed by the circular arc has a segment height of from 2.0 mm to 3.5 mm, preferably of from 2.2 mm to 2.5 mm.

It is especially conceivable for the head to have an inner diameter of from 5 mm to 10 mm, preferably of from 6 mm to 8 mm, and/or a wall thickness of from 0.2 mm to 0.6 mm, preferably of 0.4 mm. Alternatively or additionally, the head may have a depth of from 6 mm to 17 mm, in particular of from 9 mm to 14 mm, and/or the bearing element may have a length of from 10 to 19 mm, in particular of from 12 to 17 mm. In a particularly advantageous manner, the bearing element may extend 2 mm to 4 mm, in particular 3 mm, beyond the distal edge of the head in the axial direction.

In order to use the distal end of the protector device for displacing the surrounding tissue at the extraction site, the protector device may preferably be completely, but at least largely, closed at its distal end. In this case, a particular combinatorial effect is achieved with the design of the bearing element, which namely stabilizes the protector device when the outer tissue exerts pressure on the distal end of the protector device, especially in the axial direction.

In order to establish a secure connection between the protector device and the machining device, the protector device may be rotatably coupled to the shaft at its proximal end. In concrete terms, it is conceivable here for the protector device to surround the shaft in the circumferential direction.

Advantageously, the protector device can be rotatably coupled to the bearing element and/or the shaft via a sliding bearing and/or a ball bearing and/or a roller bearing. In particular, a sliding bearing is advantageous here, since this is characterized by an extremely simple and thus cost-effective design. The sliding bearing does not have to be formed as a separate element; instead, the corresponding region of the protector device or the machining device may represent the sliding bearing.

In order to prevent the processed tissue from being damaged by overheating, at least one fluid opening, for example having a diameter of approximately 0.5 mm to 0.9 mm, preferably of 0.7 mm, can be formed on the bearing element, said opening being connected to a fluid channel, for example having a diameter of approximately 0.5 mm to 1.0 mm, preferably of 0.8 mm. The fluid channel may extend from the connection region through the shaft and the bearing element to the at least one fluid opening. Thus, a cooling liquid can be introduced, for example, from the surgical handpiece, with which the surgical instrument is connected via the connection region. Since the bearing element is arranged within the hollow cylindrical head, the hollow cylindrical head and, in particular, the distal edge can ideally be exposed to cooling fluid.

In a further advantageous manner, the protector device can be made of plastic or metal. Plastic has the advantage that the protector device can be produced particularly simply and thus cost-effectively. Furthermore, a sliding bearing for connecting the protector device to the bearing element and/or the shaft can be produced in a particularly simple manner when the protector device is made of plastic. The realization of the protector device from metal offers the advantage that the protector device can be prepared again—for example in an autoclave—so that multiple use is possible.

In order to allow the surgeon a good view of the extraction site, the protector device can ideally be transparent, for example made of a transparent plastic. Alternatively or additionally, a depth marking can be formed on the outer wall of the head so that the surgeon can easily understand how deeply the head is placed into the bone to be machined. To this end for example, an especially black strip, preferably as a laser marking, may be formed on the outer wall at regular intervals. The depth marking may be formed, in particular, in increments of 1 mm to 3 mm, preferably of 2 mm.

In a particularly refined manner, at least one opening can be formed in the side wall of the head, through which the surgeon can push the extracted bone piece out of the head, for example with tweezers. The opening can be oval, for example, wherein the longest axis can be particularly 3 mm to 5 mm, preferably 4 mm.

In a further advantageous manner, a securing element made of a material, in particular of plastic, can be formed on the shaft, the shape and/or color of which changes during preparation of the instrument, for example during autoclaving. In a particularly advantageous manner, the securing element can be arranged in or on the connection region and varied, during preparation of the instrument, in such a way that the instrument can no longer be coupled to a medical handset.

BRIEF DESCRIPTION OF THE SEVERAL VIEWS OF THE DRAWINGS

There are various options for advantageously designing and developing the teachings of the present disclosure. To this end, reference is made, on one hand, to the claims and, on the other hand, to the subsequent explanation of a preferred exemplary embodiment of the disclosure by means of the drawings. Generally preferred embodiments and developments of the teachings are also explained in conjunction with the explanation of the preferred exemplary embodiment of the disclosure with reference to the drawings. The drawings show the following:

DETAILED DESCRIPTION

FIGS. 1 to 10 show, in various representations, an exemplary embodiment of a surgical instrument according to the disclosure. The surgical instrument comprises a machining device 1 which, in the exemplary embodiment shown here, is designed as a hollow bur or trephine bur. The machining device 1 comprises a shaft 2, which has a connection region 3 for coupling to a surgical handheld device, which is not shown, for example an elbow or handpiece of a dentist or dental surgeon. The machining device 1 can be set into rotation via the handheld device.

A hollow cylinder head 4 is arranged on the shaft 2. The head 4 has a distal edge 5, which is used as the active region 6 for machining and/or extracting the bone. For example, a diamond tip and/or sawing and/or cutting teeth may be formed on the distal edge 5.

A bearing element 7, which is designed as a bearing journal, extends into the head 4. In the exemplary embodiment shown, the bearing element 7 extends from the bottom 9 of the head 4 axially through the entire head 4 to beyond the distal edge 5. Specifically, the bearing element 7 is designed as an extension of the shaft 2.

Furthermore, a protector device 8 is rotatably coupled to the machining device 1. The base 10 of the protector device 8 surrounds the shaft 2 and is rotatably coupled to both the shaft 2 and the bottom 9 of the head 4; namely, the bearing element 7 may be arranged in a recess of the distal end 11. Furthermore, the distal end 11 of the protector device 8 is closed and the protector device 8 is rotatably coupled to the bearing element 7 via the distal end 11. At this point it should be noted that the coupling between the protector device 8 and the machining device 1 can also take place via a separate bearing. It is only essential that the bone can be machined and/or extracted with the rotating head 4 of the machining device 1, while the protector device 8 essentially does not rotate and protects the surrounding tissue.

Figure 1:
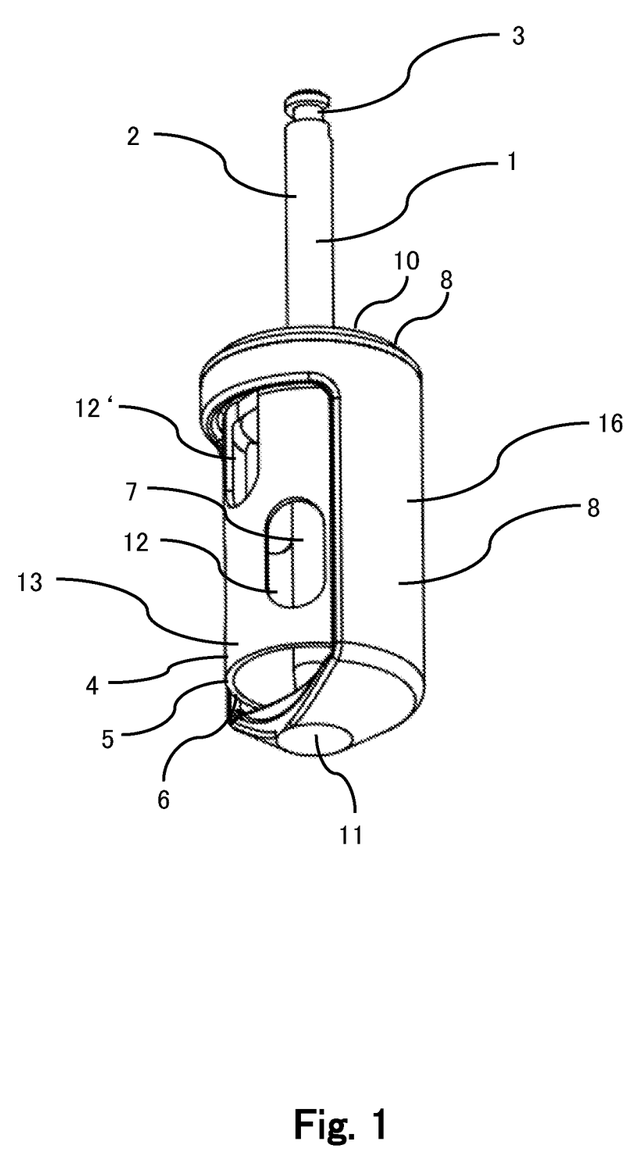
FIG. 1 shows a schematic, perspective representation of an exemplary embodiment of a surgical instrument according to the present disclosure.
Figure 2:
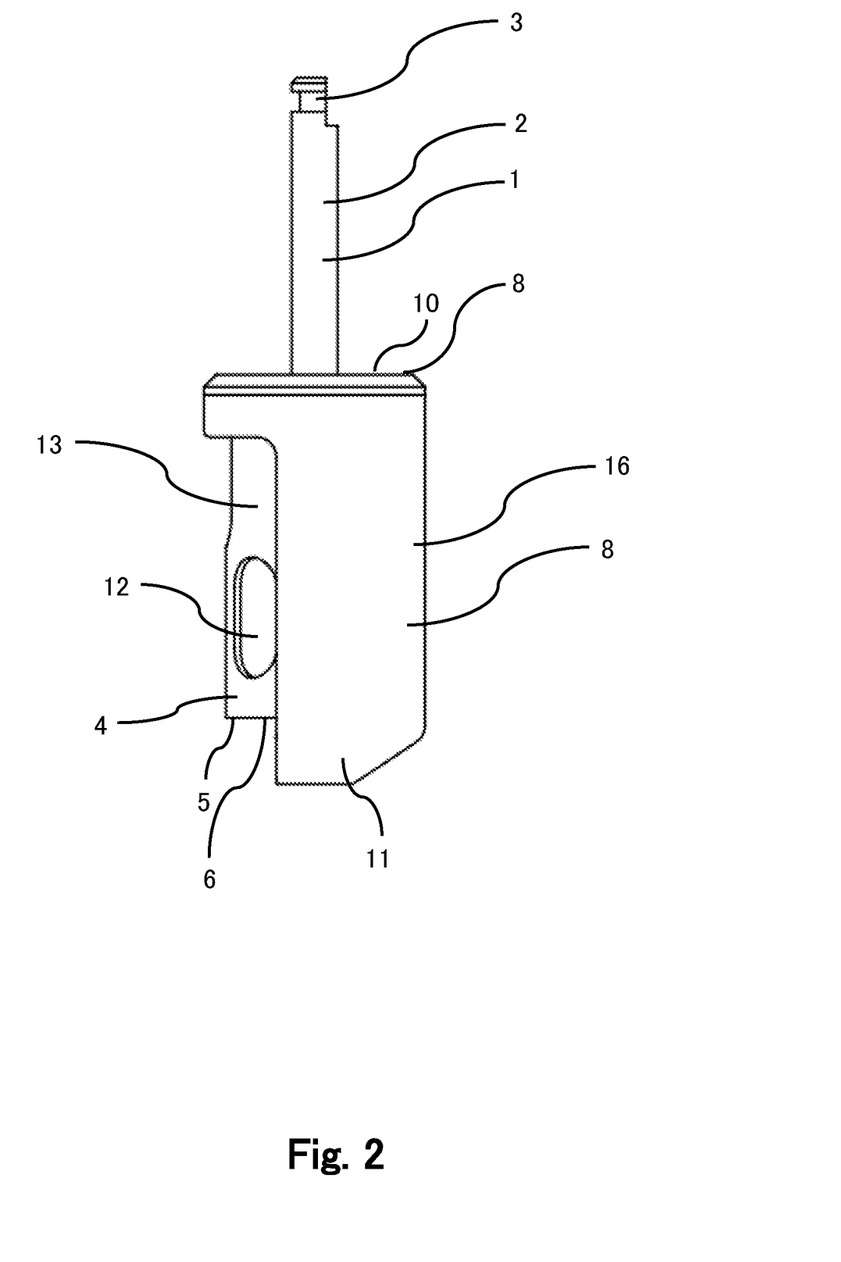
FIG. 2 shows the surgical instrument according to the disclosure from FIG. 1 in a schematic, lateral representation.
Figure 3:
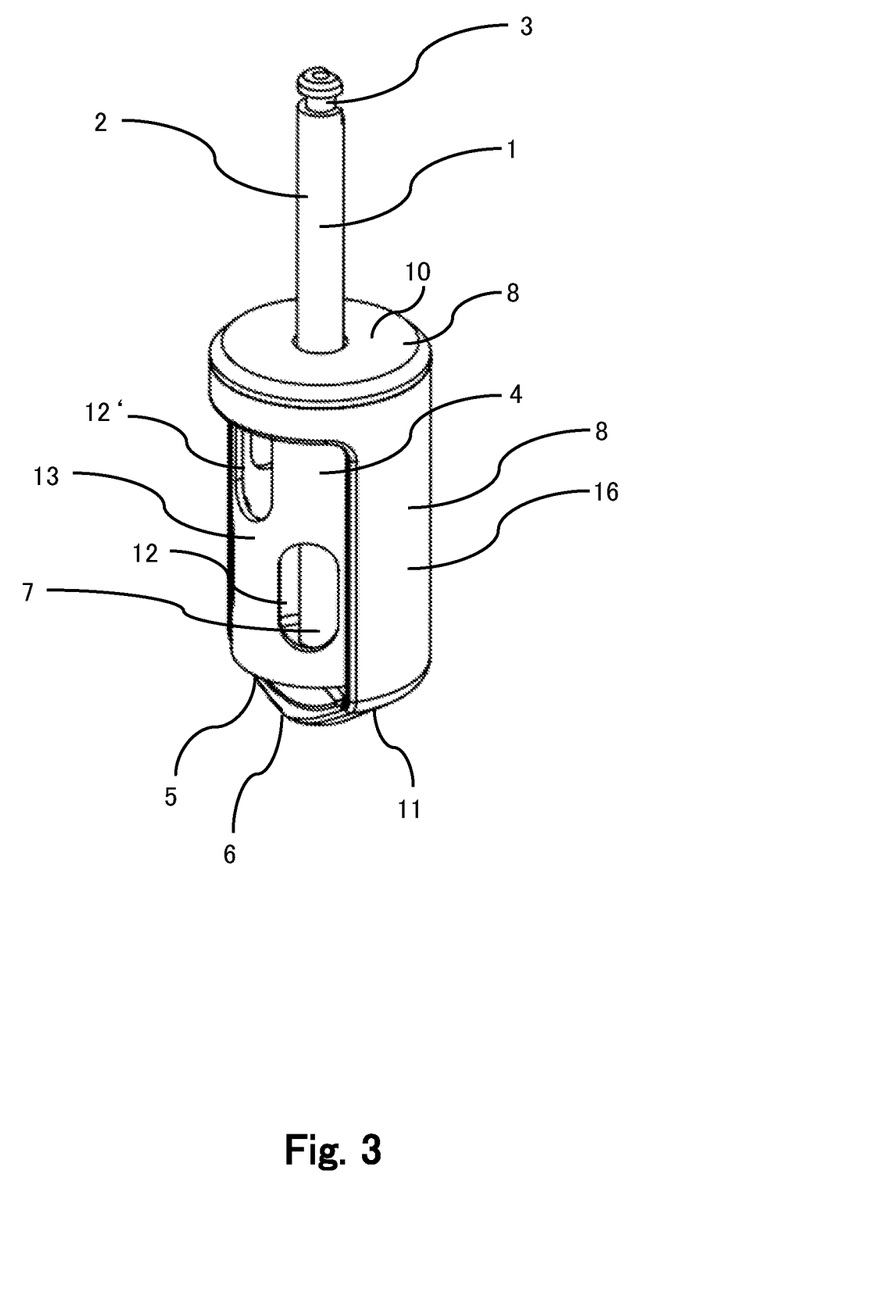
FIG. 3 shows the surgical instrument according to the disclosure from FIG. 1 in a further schematic, perspective representation.
Figure 4:
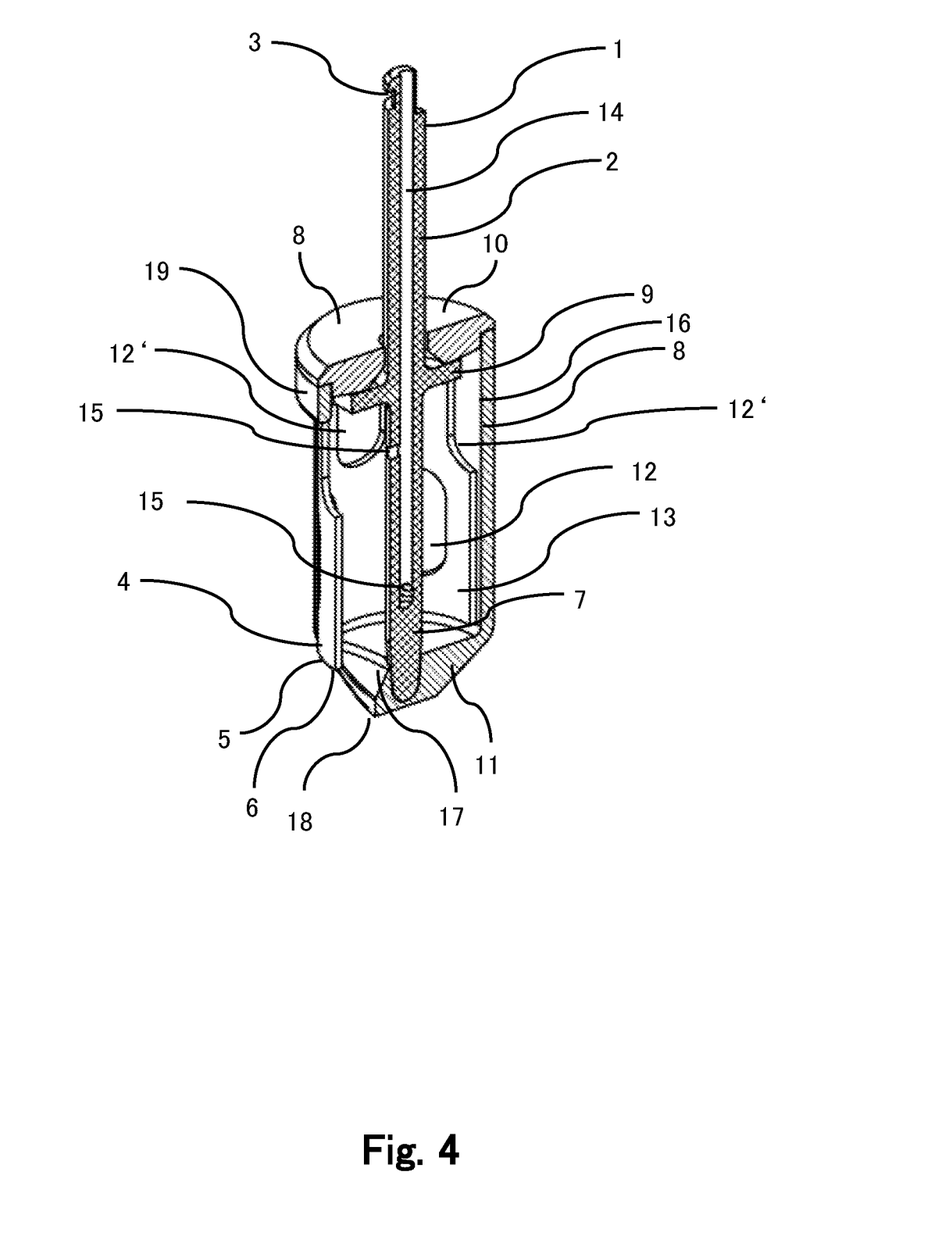
FIG. 4 shows the surgical instrument according to the disclosure from FIG. 1 in a schematic, sectional representation.

In particular, FIG. 1 clearly shows that the protector device 8 surrounds the machining device 1 such that only a circular arc of the distal edge 5 serves as the active region 6 and/or may be placed into contact with the bone to be machined. This embodiment prevents excessive penetration into the bone and protects surrounding tissue. Furthermore, it is possible for the surgeon to peel out an approximately crescent-shaped bone piece from the jaw. By coupling the distal end 11 of the protector device 8 to the bearing element 7, the distal end 11 can serve as a displacement element, with which the surrounding tissue can be displaced during engagement. In particular, FIG. 5 clearly shows that an oblique 17 is formed at the distal end 11. The oblique 17 simplifies the extraction of the bone segment from the head 4. Thus, the distal end 11 in the region of the oblique 17 is sufficiently solid, reducing the diameter of the bearing element 7 at its end. It should also be noted that the corner region 18 of the distal end 11 may be rounded in order to prevent tilting of the protector device 8.

Figure 5:
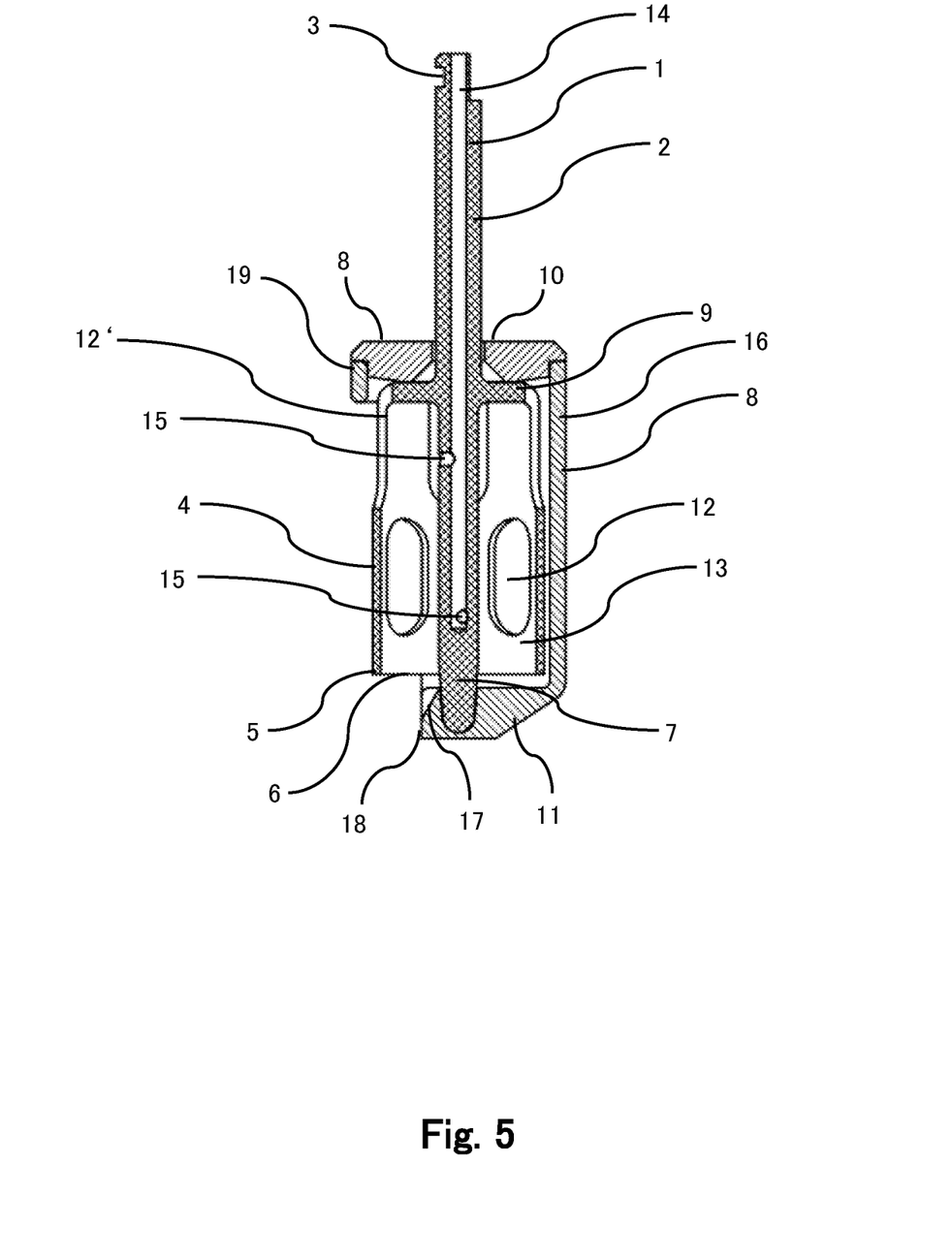
FIG. 5 shows the surgical instrument according to the disclosure from FIG. 1 in a further schematic, sectional representation.
Figure 6:
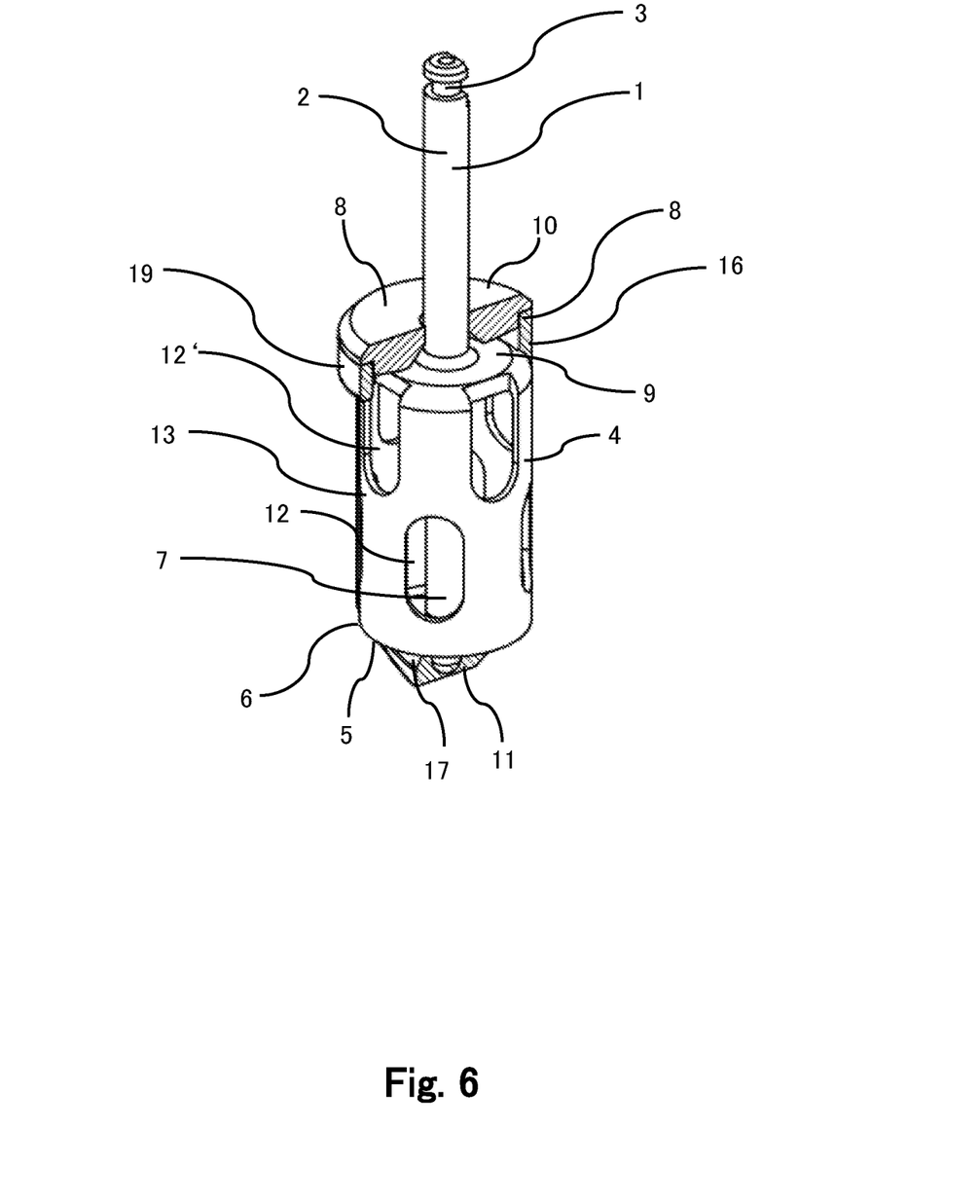
FIG. 6 shows the surgical instrument according to the disclosure from FIG. 1 in a schematic, partially sectional representation.
Figure 7:
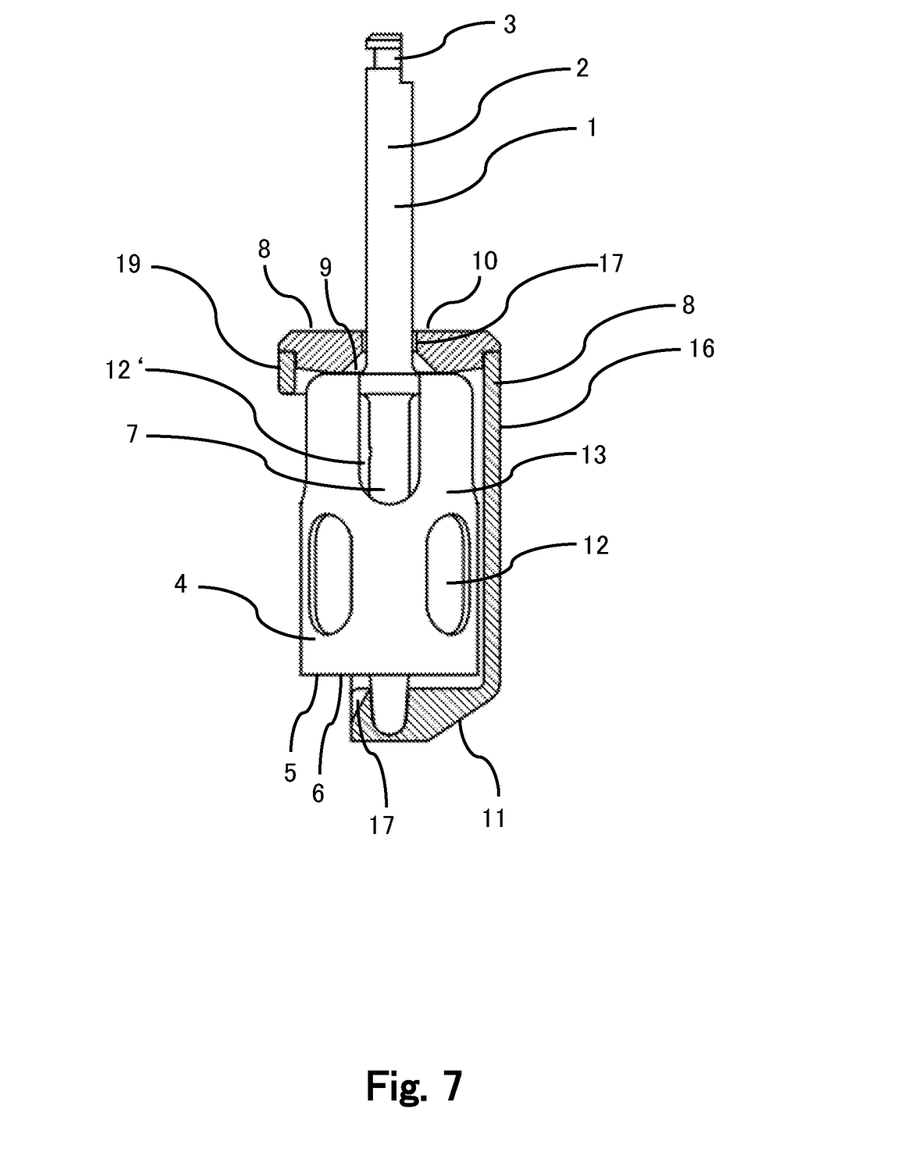
FIG. 7 shows the surgical instrument according to the disclosure from FIG. 1 in a further schematic, partially sectional representation.
Figure 8:
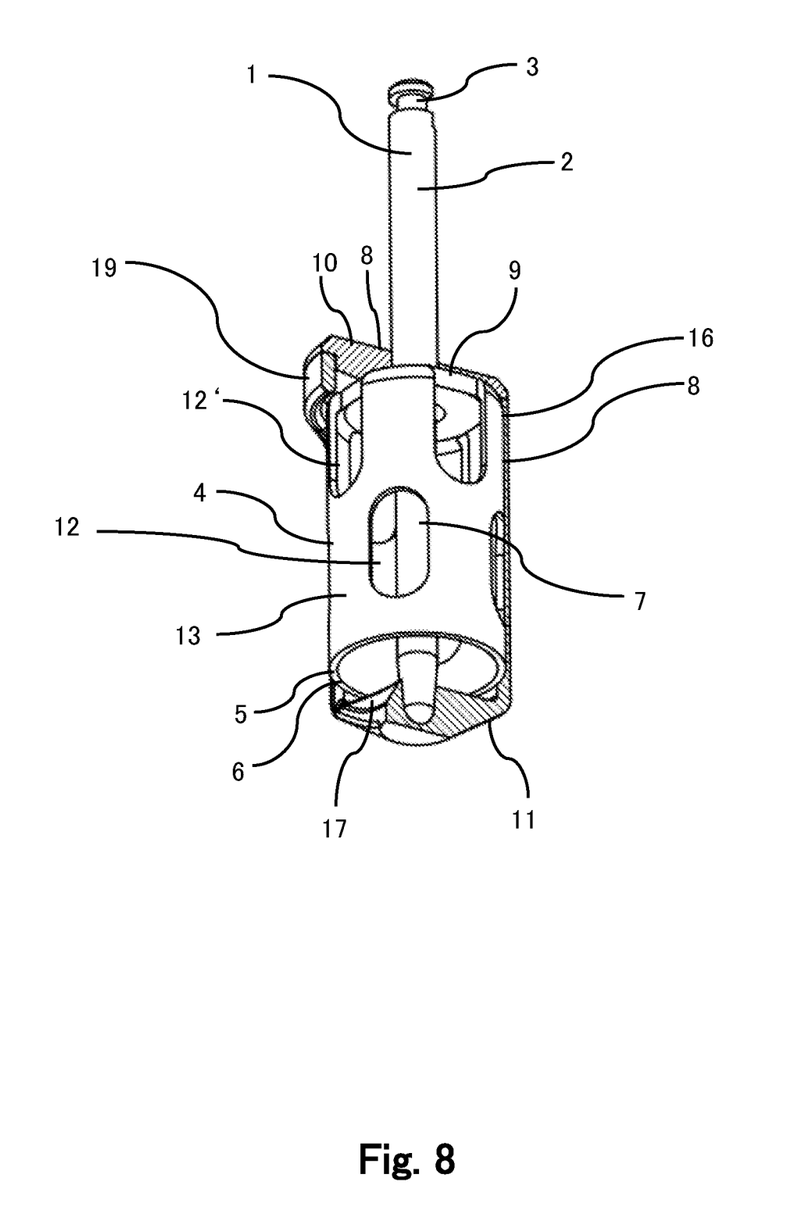
FIG. 8 shows the surgical instrument according to the disclosure from FIG. 1 in a further schematic, partially sectional representation.

To extract the circular-segment-shaped bone piece from the head 4, openings 12 are formed in the side wall 13 of the head 4. The surgeon can thus push the loosened bone piece out of the head 4 through the opening 12—for example with tweezers or a similar tool. FIG. 5 clearly shows that the opening 12' extends up to the bottom 9 of the head, so that the extracted bone segment can be pushed out of the head 4, in a particularly simple manner, with a separate instrument. In order to simplify this again, the edge 19 of the cylinder element 16 terminates in the axial direction with the bottom 9 of the head 4.

In order to cool the engagement point, a fluid channel 14 is formed, which extends from the connection region 3 through the shaft 4 and the bearing element 7. In particular, FIG. 5 clearly shows that two fluid openings 15 are formed in the bearing element 7, which are in contact with the fluid channel 14 so that cooling fluid can be conveyed from the surgical handpiece to the fluid openings 15 via the connection region 3 and the fluid channel 14. The cooling liquid is sprayed from the fluid openings 15 onto the head 4 and/or the extraction site located behind it.

Figure 9:
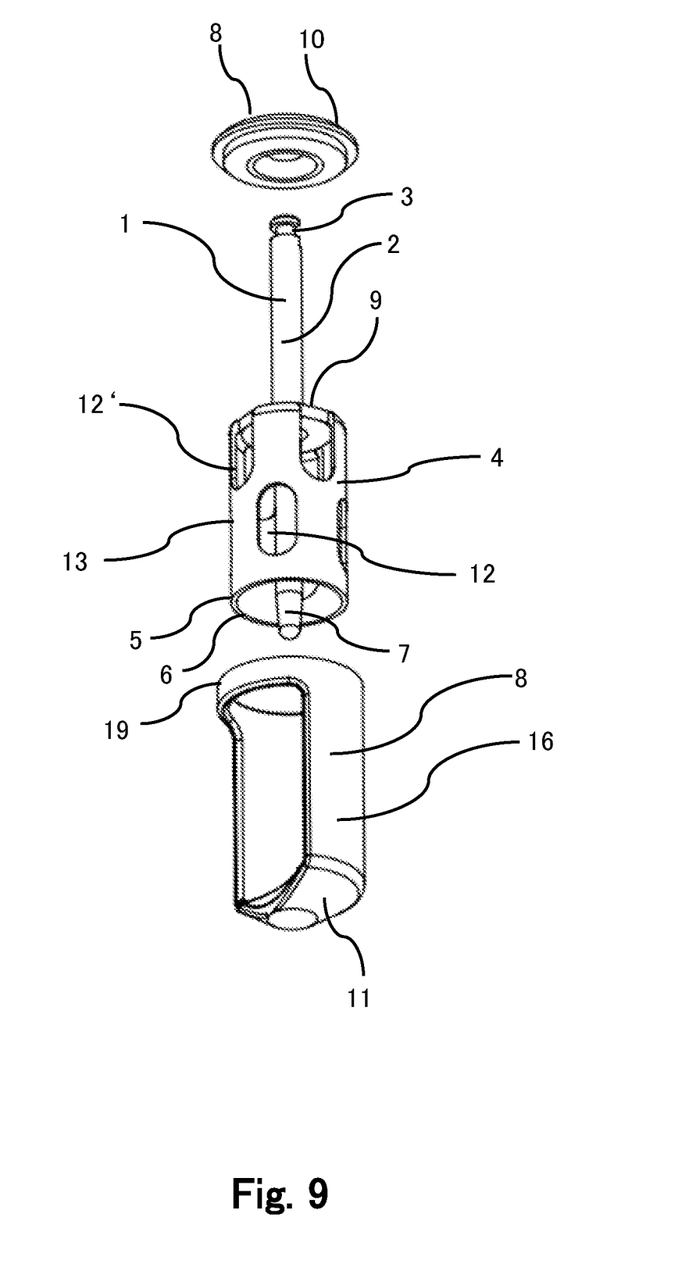
FIG. 9 shows the surgical instrument according to the disclosure from FIG. 1 in a schematic, perspective exploded view.
Figure 10:
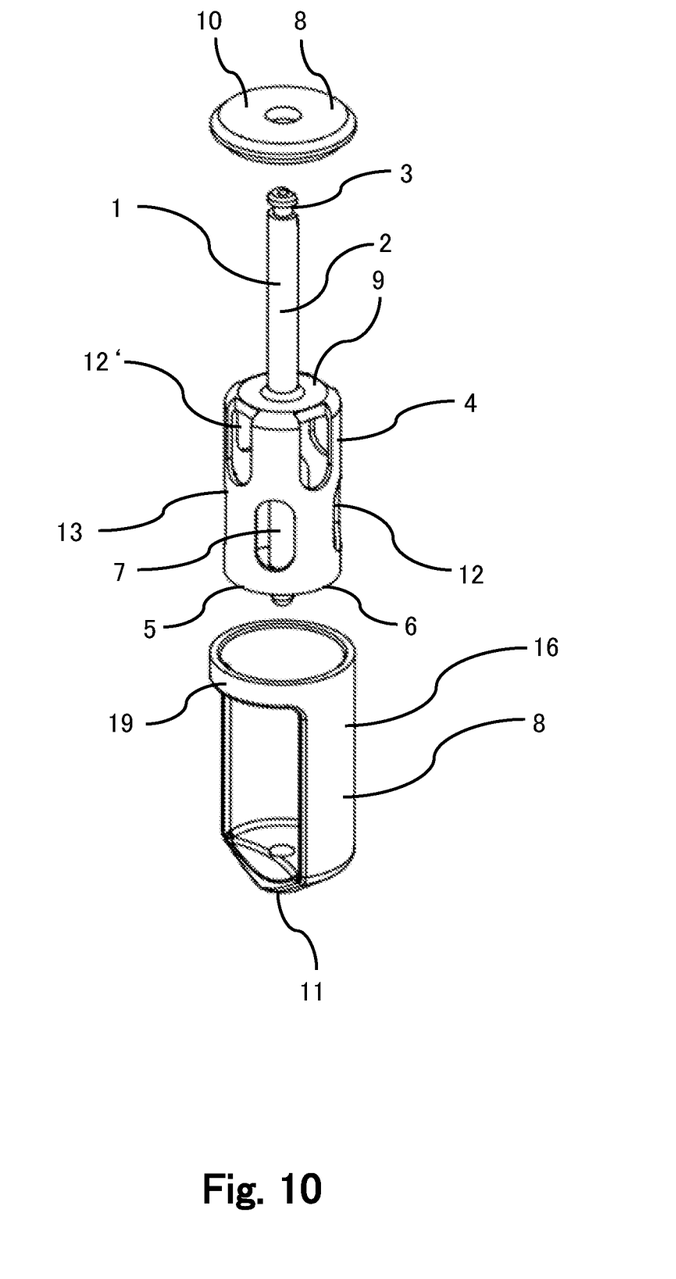
FIG. 10 shows the surgical instrument according to the disclosure from FIG. 1 in a further schematic, perspective exploded view.

As can be seen in particular from FIGS. 9 and 10, the protector device 8 is embodied in two parts in the exemplary embodiment shown here, namely having a base 10 and a cylinder element 16. The base 10 and the cylinder element 16 can be interconnected using positive-locking and/or friction-locking and/or bonding, for example screwed, clamped, glued, ultrasonically welded, etc. The base 10 of the protector device 8 can advantageously lie flat, at least in regions, on the bottom 9 of the head 4 in an advantageous manner.

With regard to other advantageous embodiments of the device according to the disclosure, to avoid repetition, reference is made to the general part of the description and also to the accompanying claims.

Finally, it is expressly pointed out that the above-described exemplary embodiments of the device according to the disclosure serve only to explain the claimed teaching, but do not limit it to the exemplary embodiments.

LIST OF REFERENCE SYMBOLS

1 Machining device
2 Shaft
3 Connection region
4 Head
5 Distal edge (head)
6 Active region
7 Bearing element
8 Protector device
9 Bottom (head)
10 Base (protector device)
11 Distal end (protector device)
12, 12' Opening (head)
13 Side wall
14 Fluid channel
15 Fluid opening
16 Cylinder element
17 Oblique 18 Corner region
19 Edge The various embodiments described above can be combined to provide further embodiments. These and other changes can be made to the embodiments in light of the above general description and detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A surgical instrument, for use in dental surgery, comprising:
   a machining device; and
   a protector device,
   wherein the machining device has a shaft with a connection region and a hollow cylindrical head, wherein an active region for machining and/or grinding of bone is formed at a distal edge of the head, and
   wherein:
      the distal edge of the head is circular,
      the protector device at least partially surrounds the head such that only a circular arc of the distal edge of the head acts as the active region for machining and/or grinding of bone, and
      the protector device is rotatably coupled to a bearing element of the machining device, which bearing element extends, at least partially, inside of the head.

2. The surgical instrument according to claim 1, wherein the bearing element extends in an axial direction from a bottom of the head at least up to the distal edge of the head.

3. The surgical instrument according to claim 1, wherein the bearing element extends axially beyond the distal edge of the head.

4. The surgical instrument according to claim 1, wherein the bearing element is in the shape of a pin.

5. The surgical instrument according to claim 1, wherein the protector device is coupled to the bearing element at a distal end of the protector device.

6. The surgical instrument according to claim 1, wherein a distal end of the protector device is closed.

7. The surgical instrument according to claim 1, wherein the protector device is rotatably coupled to the shaft at a proximal end of the protector device.

8. The surgical instrument according to claim 1, wherein the protector device is rotatably coupled to the bearing element and/or the shaft via a sliding bearing, a ball bearing, and/or a roller bearing.

9. The surgical instrument according to claim 1, wherein at least one fluid opening, which is connected to a fluid channel, is formed on the bearing element, wherein the fluid channel extends from the connection region through the shaft and the bearing element to the at least one fluid opening.

10. The surgical instrument according to claim 1, wherein the protector device is made of plastic or metal.

11. The surgical instrument according to claim 1, wherein the protector device is transparent.

12. The surgical instrument according to claim 1, wherein at least one opening is formed in a side wall of the head through which machined and/or ground bone can be extracted from the head.

* * * * *